United States Patent
Elver et al.

(10) Patent No.: US 6,464,671 B1
(45) Date of Patent: Oct. 15, 2002

(54) MEDICAL SYSTEM

(76) Inventors: Sten-Olof Elver, Hästängsuddvägen 22, S-184 92 Åkersberga (SE); Jan Skansen, Box 8, S-134 06 Ingarö (SE)

( * ) Notice: Subject to any disclaimer, the term of this patent is extended or adjusted under 35 U.S.C. 154(b) by 0 days.

(21) Appl. No.: 09/532,522

(22) Filed: Mar. 21, 2000

Related U.S. Application Data
(60) Provisional application No. 60/152,608, filed on Sep. 8, 1999.

(30) Foreign Application Priority Data

Apr. 28, 1999 (SE) ............................................. 9901528
May 4, 1999 (SE) ............................................. 9901608

(51) Int. Cl.[7] ............................................. A61M 31/00
(52) U.S. Cl. ............... 604/288.01; 604/131; 604/890.1; 604/93.01; 604/288.01; 604/288.04
(58) Field of Search ................ 604/131, 140, 604/141, 151, 153, 200, 890.1, 891.1, 892.1, 93.01, 502, 500, 67, 148, 288.01, 288.02, 288.03, 288.04; 128/DIG. 12

(56) References Cited

U.S. PATENT DOCUMENTS

| | | | |
|---|---|---|---|
| 3,692,027 A | * 9/1972 | Ellinwood, Jr. | 128/260 |
| 4,193,397 A | 3/1980 | Tucker et al. | |
| 4,265,241 A | * 5/1981 | Portner et al. | 128/260 |
| 4,443,218 A | * 4/1984 | DeCant, Jr. et al. | 604/67 |
| 4,673,391 A | 6/1987 | Kondo et al. | |
| 4,781,688 A | * 11/1988 | Thoma et al. | 604/132 |
| 4,871,351 A | 10/1989 | Feingold | |
| 5,041,094 A | 8/1991 | Perego | |
| 5,085,656 A | 2/1992 | Polaschegg | |
| 5,368,588 A | 11/1994 | Bettinger | |
| 5,575,770 A | * 11/1996 | Melsky et al. | 604/93 |
| 5,607,418 A | 3/1997 | Arzbaecher | |
| 5,643,207 A | * 7/1997 | Rise | 604/93 |
| 5,695,490 A | * 12/1997 | Flaherty et al. | 604/891.1 |
| 5,752,930 A | 5/1998 | Rise et al. | |
| 5,769,823 A | * 6/1998 | Otto | 604/141 |

FOREIGN PATENT DOCUMENTS

| | | |
|---|---|---|
| EP | 0 429 141 | 5/1991 |
| EP | 0 672 427 | 9/1995 |
| WO | WO 95/29717 | 11/1995 |

* cited by examiner

Primary Examiner—Brian L. Casler
Assistant Examiner—Cris L. Rodriguez
(74) Attorney, Agent, or Firm—Young & Thompson

(57) ABSTRACT

Implantable drug delivery system comprising a reservoir module provided with a drug reservoir and a drug expelling means arranged to expel a drug from said drug reservoir, and a dispenser module comprising drug delivery means having a predetermined number of drug delivery openings for delivering a drug, received from said drug reservoir, to tissue. The modules are physically separate parts and the reservoir module is provided with a first connecting means and the dispenser module is provided with a second connecting means, wherein, at the time of implantation, the modules are adapted to be connected together by the first and second connecting means.

10 Claims, 8 Drawing Sheets

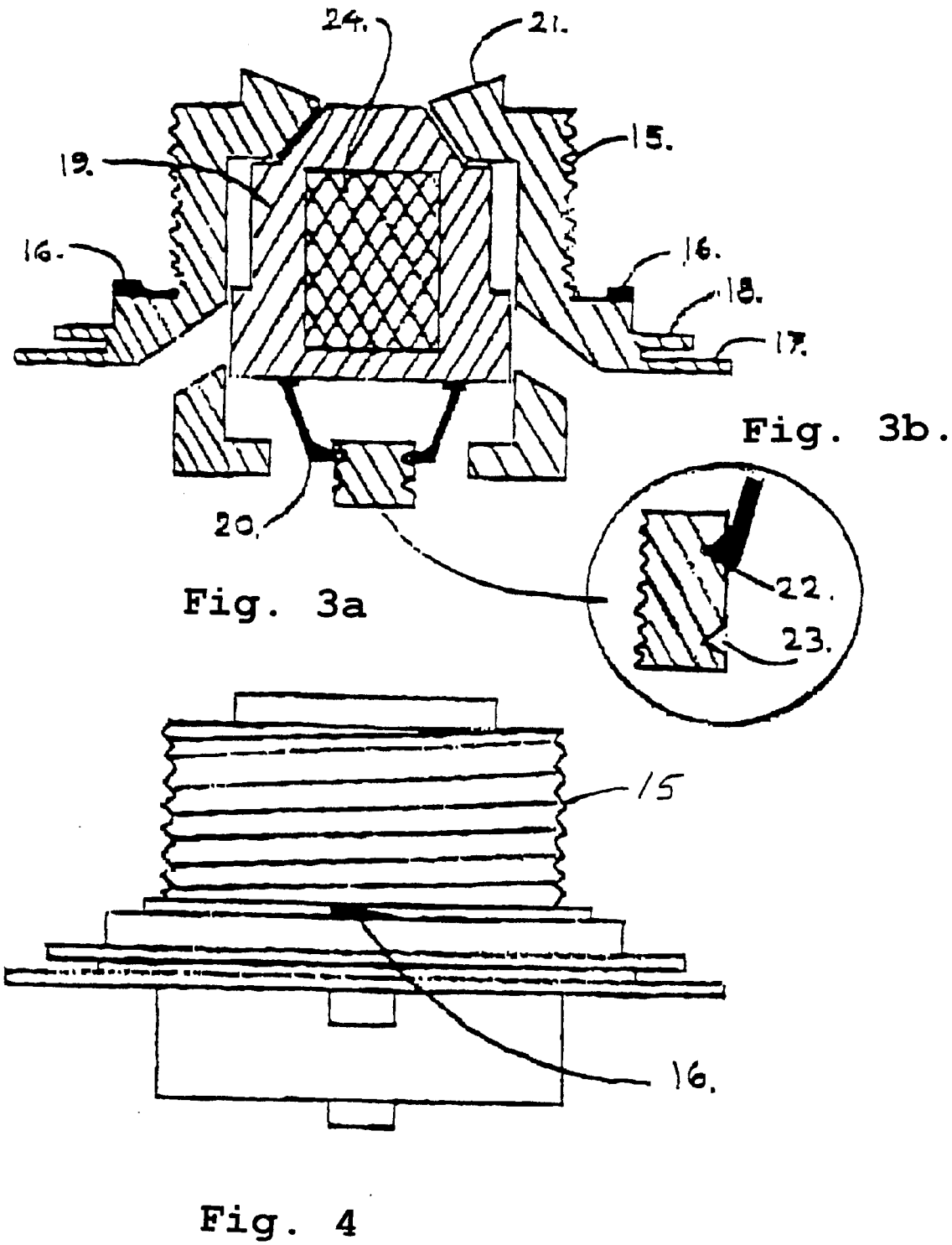

MEDICAL SYSTEM

TECHNICAL FIELD OF THE INVENTION

The present invention relates to an implantable drug delivery system, a dispenser module, a set of dispensing modules, a reservoir module, a set of reservoir modules and a method of administrating a drug using the implantable drug delivery system according to the preamble of the independent claims.

BACKGROUND OF THE INVENTION

1. Field of the Invention

Pharmaceutical drugs can be administrated to patients in many different ways, such as orally, nasally, through electroporation or by injections. Injections can be intravenous, intramusculaire or subcutaneous. The way of administration of drugs to a patient is often depending on properties of the drug, the organ to be treated and the patient's physical and social presumptions to control the prescribed treatment. The efficiency of the prescribed drug treatment is also highly dependent on the patient's abilities to follow the prescription. It is a well-known fact that the ability to follow a prescription is related to the patient's understanding and knowledge of his disease and his possibility to follow the prescribed form of treatment.

Medical treatment by subcutaneous injections during a long period of time in patients that due to physical or social reasons themselves cannot make the injection are requiring assistance from e.g. a nurse or a relative.

The injection itself might have considerable side effects because a relatively high concentration of an active substance is administrated to one local site beneath the skin. Irritation of the skin or local haematoma is common for some patients.

Parameters that affect how frequent the injections are taken are the subcutaneaous half-life time for the drug, i.e. the time it takes for half the injected dose to be absorbed by tissue, the actual dose and of course the patient's ability to follow the prescription.

The injected volume depends on the type of drug used and the wanted effect of the treatment and is normally between 0,2–0,6 ml per day given in 1–3 injections.

The costs to offer sterilized injection syringes and to discard them after use is a considerable part of the total cost for the treatment.

2. Description of the Prior Art

Implantable infusion pumps are well known in the art for administrating drugs to a patient, e.g. to administer insulin to the pancreas, pain-relieving drugs to the spinal canal or intravenous administration of drugs against Parkinson's disease. Below is a short summary of different kinds of implantable infusion pumps U.S. Pat. No. 4,193,397 discloses an implantable infusion apparatus and method. Although mentioned the possibility of having a battery powered electrical valve to perform the pumping action, a preferred pump embodiment employs a valve that can be actuated extracorporeally either manually or magnetically. Modifying the flow rates and volumes of the apparatus components, particularly the mixing chamber and the apparatus outlet tube, can provide a dosage profile tailored to the patient's requirements. The described embodiment requires the patient's contribution that, according to the discussion above, is a major drawback.

Also U.S. Pat. No. 5,769,823 discloses an implantable infusion pump. The purpose of this known device is primarily to provide an inexpensively manufacturable infusion pump. This is accomplished by arranging a plastic casing with a bellows that receives a propellant producing a vapour pressure that exerts a pressure on two resilient bags containing a medicament. When a throttle means is opened a clearly defined quantity of the medicament passes out of the bags into a catheter and into the body of a patient.

U.S. Pat. No. 4,673,391 discloses a micropump disposed within a human body for continuously delivering small quantities of a pharmaceutical liquid stored therein to be injected in a human body. The control part of the pump is placed outside the body and generates a magnetic force that can open a valve of the implanted micropump and release the pharmaceutical liquid. A problem with this known device is that it requires that the patient actively controls the device, which not always is possible or desirable.

U.S. Pat. No. 5,752,930 relates to an implantable infusion pump for administration of a pharmaceutically active agent via a catheter to a plurality of infusion sites located at spaced intervals in a portion of a body to be treated by the agent. The catheter is provided with elution holes to perform the administration of the agent. However, experience has shown that the flow rate of the agent is not uniform through all elution holes. In particular, at low flow rates, fluid moving down the catheter exits the catheter at the elution hole having the least fluid resistance to flow to that relatively little or no fluid exits the catheter through the remaining elution holes. This results in overdose to some sites (the elution hole with the least fluid resistance) and underdose to other sites (remaining elution holes). The device described in U.S. Pat. No. 5,752,930 is directed to solve that problem. The solution is shortly to apply a first pressure to the agent in the catheter for a first time period and a second pressure to the agent for a second time period so that substantially the same dosage of agent can be applied to each of the sites. One drawback with this solution is that it is technically rather complicated in that it requires an accurate control of the applied pressure.

One major drawback with implantable infusion pumps according to the prior art is that they cannot easily be optimized with regard to flow-rate of the delivered drug and the volume of drug stored in the pump.

Another drawback with the prior art infusion pumps is that they have a complicated structure inter alia due to that they all administer the drug via a catheter.

SUMMERY OF THE INVENTION

It is an object of the present invention to provide an implantable drug delivery system where the above-mentioned drawbacks are avoided. These drawbacks are avoided by the implantable drug delivery system, a dispenser module, a set of dispensing modules, a reservoir module, a set of reservoir modules and a method of administrating a drug using the implantable drug delivery system according to the independent claims. Preferred embodiments are set forth in the dependent claims.

The present invention makes it possible to tailor the treatment by choosing a reservoir module and a dispenser module having a desired performance for achieving an optimal treatment, i.e. the possibility to administer a prescribed dose during a prescribed time in a controlled manner.

The invention is especially useful for short term implantation for administration of drugs during some weeks or month after a surgery, e.g. related to hip or knee prosthesis, when the patient is immobilized during the recovery period.

The drug is delivered to tissue through drug delivery openings that are arranged around the periphery of the dispenser module. At least two openings are provided. In order to provide an easy-handled implantable infusion system the drug delivery openings are arranged around the periphery of the implant. This is advantageous in that no delivery catheter is needed according to a preferred embodiment of the invention.

By arranging several openings a most advantageous drug delivery is achieved in that only a limited volume is delivered at each location which is favorable in that the risk of negative effect on tissue as a result of too high drug exposure is almost eliminated. An ideal situation exists if the limited volume delivered from one opening is in a one to one relationship with the absorption at the delivery site. In other word if the capillary force of the tissue at the delivery site provides for continuous absorption of all delivered drug at the delivery site then the ideal situation occurs. Furthermore, according to still another embodiment of the invention, it is possible to only use some of the delivery openings and according to predetermined pattern "activate" different openings at different times.

The drug supplying means comprises drug delivery channels, which is a system of channels for providing the delivery openings with drug. In an implantable drug delivery system it is of greatest importance to know the exact volume of the delivered drug dose. However, in a system with a drug delivery channel having several openings of the same size arranged along a channel with the same inner diameter along the channel the pressure inside the channel changes along the channel. This pressure change results in a gradually decreasing delivered volume when approaching the distal end of the channel (the end most far from the drug reservoir). In order to arranged a system where the delivered volume is controllable and almost the same for all openings the area of the openings increases along the channel towards the distal end according to a predetermined relationship.

It is also possible to arrange a separate delivery channel for each delivery opening. In that case and if they have the same length then the area of the separate openings can be same resulting in that the same volume is delivered from each opening.

BRIEF DESCRIPTION OF THE DRAWINGS

FIG. 3 shows cross-sectional view of the reservoir nipple according to the present invention;

FIG. 4 shows a side view of the reservoir nipple according to the present invention;

DESCRIPTION OF THE PREFERRED EMBODIMENTS

Figure 1:
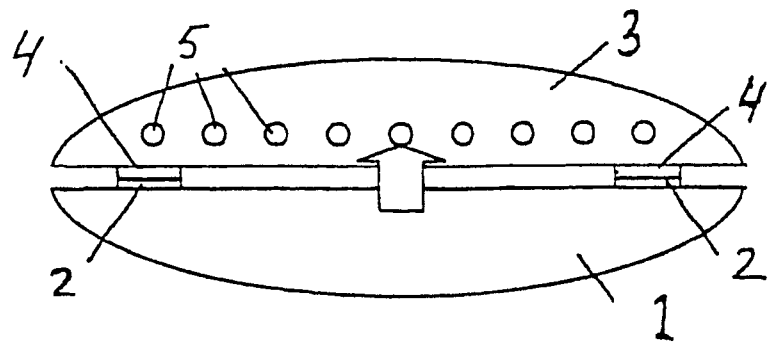
FIG. 1 shows a schematic drawing of the implantable system illustrating the functional principles of the present invention.

The functional principles of the present invention are illustrated by the schematic drawing disclosed in FIG. 1. FIG. 1 shows a reservoir module 1 provided with first connecting means 2 and a dispenser module 3 provided with second connecting means 4. Drug delivery openings 5 are arranged along the periphery of the dispenser module. The arrow schematically designates the flow of drug from the reservoir module to the delivery openings of the dispenser module. The modules are physically separate parts that, at the time of implantation, are adapted to be connected together by the first and second connecting means.

Figure 2:
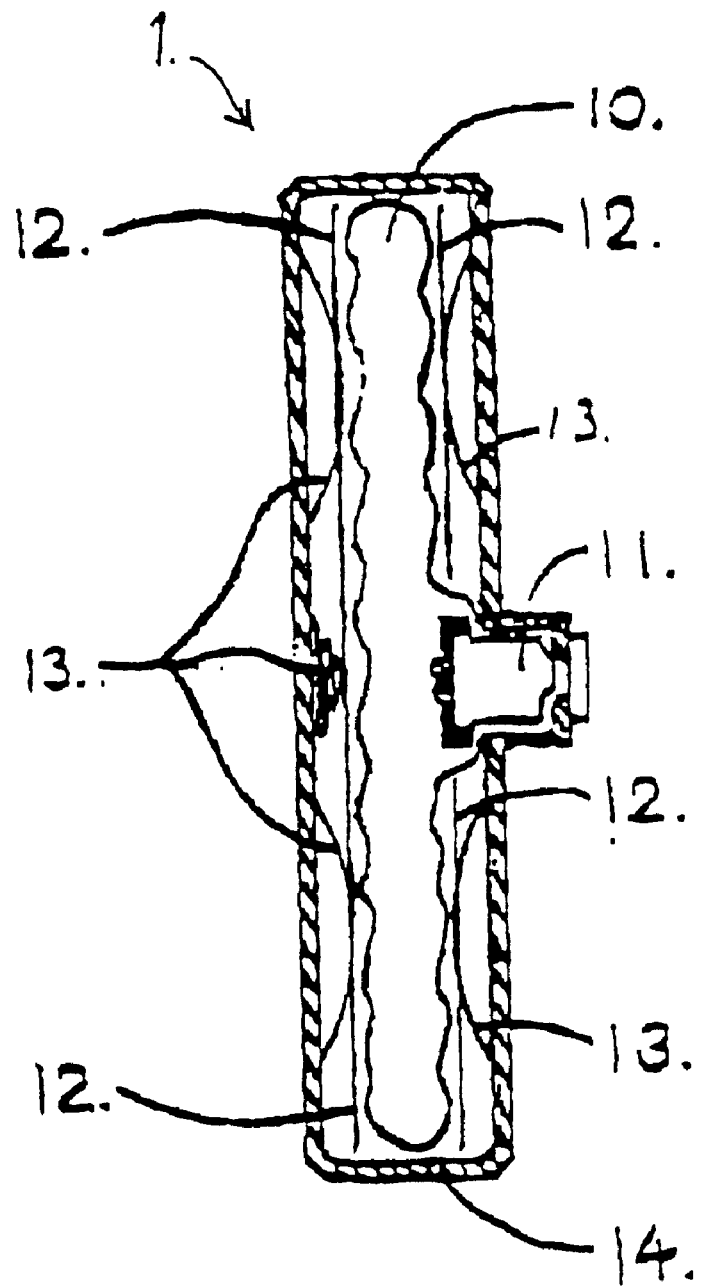
FIG. 2 shows a cross-sectional view of the reservoir module according to the present invention.

FIG. 2 shows a cross-sectional view of the reservoir module according to a preferred embodiment of the present invention. The reservoir module 1 comprises a drug reservoir 10 with a reservoir opening provided with a drug supplying means which in this embodiment is illustrated as a nipple including an interior valve 11, drug expelling means 12,13 and a protective casing 14 enclosing the reservoir and the expelling means. The drug supplying means supplies the dispenser module with a pharmaceutical drug as will be described in greater detail below. The protective casing is made from an inert material having biocompatible characteristics, such as titanium, stainless steel or a composite of polymers. The drug reservoir 10 is compressible and elastic and made of an inert treated aluminum-laminated foil, rubber, silicone or a polymer e.g. PVC. The material used inside the reservoir is of course approved by the authorities for use in contact with each pharmaceutical drug to be stored. The drug expelling means 12,13 can be arranged in many different ways. The main function of the drug expelling means is to exert a force on the drug reservoir so that drug is expelled therefrom. One preferred way of achieving the necessary force is illustrated in FIG. 2. One or many movable plate(s) are arranged to provide a pressure on the drug reservoir. The pressure that makes the plates to move are in turn generated by a number of springs that provide for a constant mechanical force on the plate(s). As can be seen from the figure, both helix-wounded springs and spring leaves can be used. Also temperature dependent bimetal springs or a foam rubber are possible to use. Another possibility, as shown in the prior art, see e.g. the above-mentioned U.S. Pat. No. 4,673,391 or U.S. Pat. No. 5,769,823, is to use a liquid or a gas to exert the pressure on the reservoir.

With references to FIGS. 3 and 4 the reservoir nipple including an interior valve will now be described.

The reservoir nipple is manufactured in an inert material, as titanium, glass, gold or a gold/platinium plated material or a polymer e.g. PVC, with a threaded outside 15 and with two stop protrusions 16, that prevent unscrewing the reservoir module from the dispenser module when connected together. The reservoir nipple further comprises a profiled area 17 to fixate the collapsible inner reservoir around by a shrinking process, a supporting area 18 where the protective casing is attached by welding, a valve 19 with two suspended claws 20 in the low end of the valve. The top of the nipple is angled so that an injection needle can be guided towards the upper part of the valve 21. On the lower part of the nipple two grooves 22,23 are made to create two distinct positions for the valve's suspended claws. The inner reservoir, prior to being filled for the first time, is free of air e.g. in vacuum, as the valve is locked into its upper position where the valve is closed (this upper position shown in FIG. 3). The valve is locked in this position by the friction of the suspended claws to the upper groove, which friction is higher than surrounding air pressure allowing no air to enter the inner reservoir. When filling is about to take place, the injection needle pushes the valve to its lower position, in which the valve is open, and the suspended claws attach to the lower groove, allowing the vacuum pressure to assist in filling the inner reservoir to its fullest extend.

It is important to have the possibility to control the valve from outside the body when the device is implanted, i.e. to be able to close the valve in order to stop the liquid distribution and also to reopen it when desired.

One way to control the valve is by arranging a magnet into the valve 24 making it possible with the aid of a strong external magnet to close, if needed, the distribution of liquid from the inner reservoir. An alternative method of closing liquid distribution after implantation is to have the valve mounted on a central bar equipped with a spiral spring. This bar has one thread with one stable position where the valve is open to allow liquid to flow to the dispenser module. By pushing the valve with the tip of an injection needle the valve is brought out of its stable position closing the liquid flow. The principle is analogous to how a ball pen with a push function works. A second push by an injection needle allows the valve to enter its stable position, whereby the flow can continue after a temporary stop.

As described in connection with FIG. 1 is the reservoir module connected to the dispenser module by first and second connecting means. As briefly discussed above is the drug supplying means arranged in the reservoir module and adapted to be coupled to the dispenser module in order to supply the dispenser module with the drug from the reservoir module. According to a preferred embodiment of the present invention (as described with references to FIGS. 2–4) is the first and second connecting means integrated with the drug supplying means. It is of course also possible to arrange the first and second connecting means separate from the drug supplying means (as indicated in FIG. 1).

Figure 5:
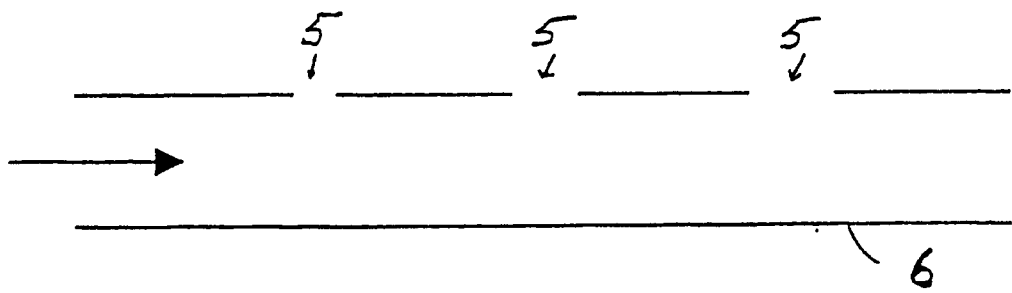
FIG. 5 shows a schematic drawing illustrating a delivery channel according to one embodiment of the invention.

The drug supplying means is connected to drug delivery channels in order to deliver the drug to the openings of the dispenser module. In order to arranged a system where the delivered volume is controllable and preferably the same for all openings the area of the openings increases along the channel towards the distal end according to a predetermined relationship. This is roughly disclosed in FIG. 5 where the delivery channel 6 and drug delivery openings 5 are shown. As can be seen increases the area of the openings along the channel in the direction of the drug flow (see arrow in the figure).

It is also possible to arrange a separate delivery channel for each delivery opening. In that case and if the channels have the same length then the area of the separate openings can be same resulting in that the same volume is delivered from each opening.

According to a preferred embodiment of the invention is a combination of the above-mentioned principles of arranging the delivery channel used.

Figure 6:
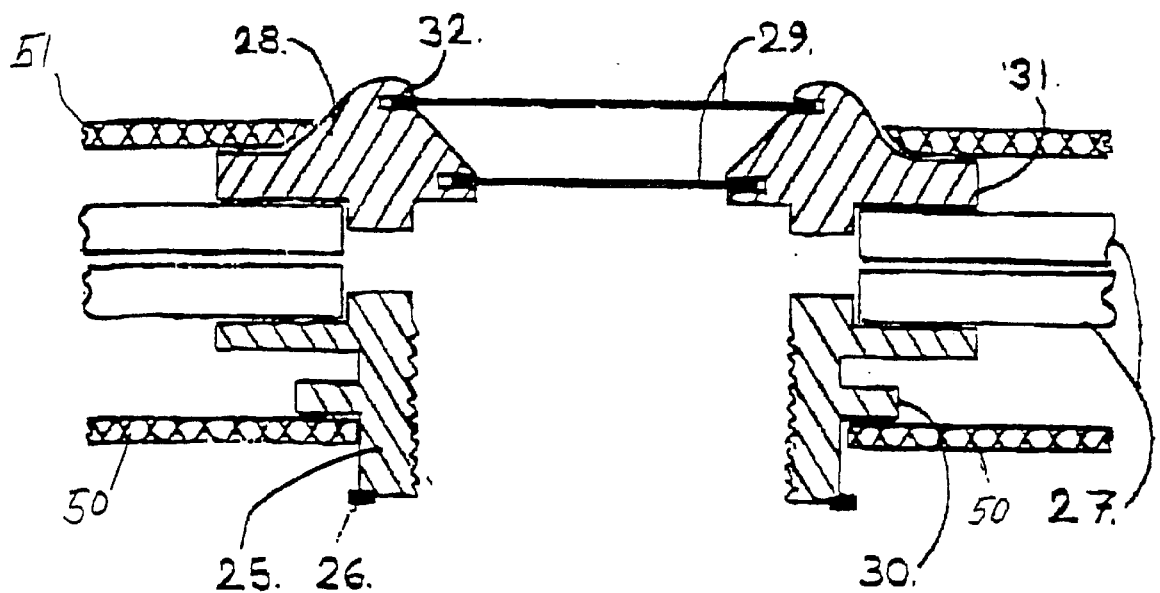
FIG. 6 shows a cross-sectional view of a connecting nipple of the dispenser module according to the present invention.
Figure 7:
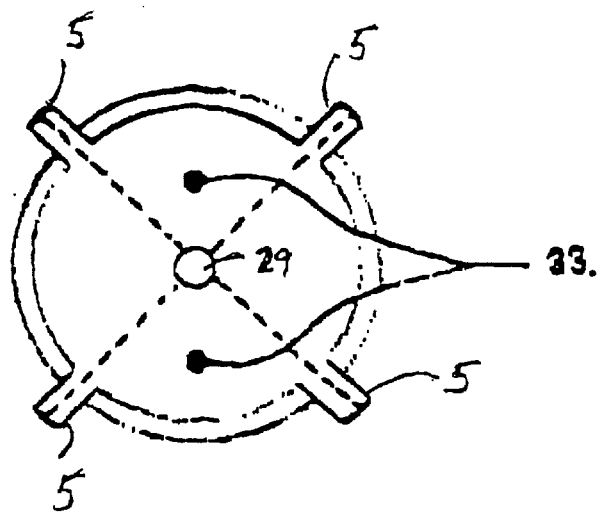
FIG. 7 shows a top view of the dispenser module according to a preferred embodiment of the invention.
Figure 8:
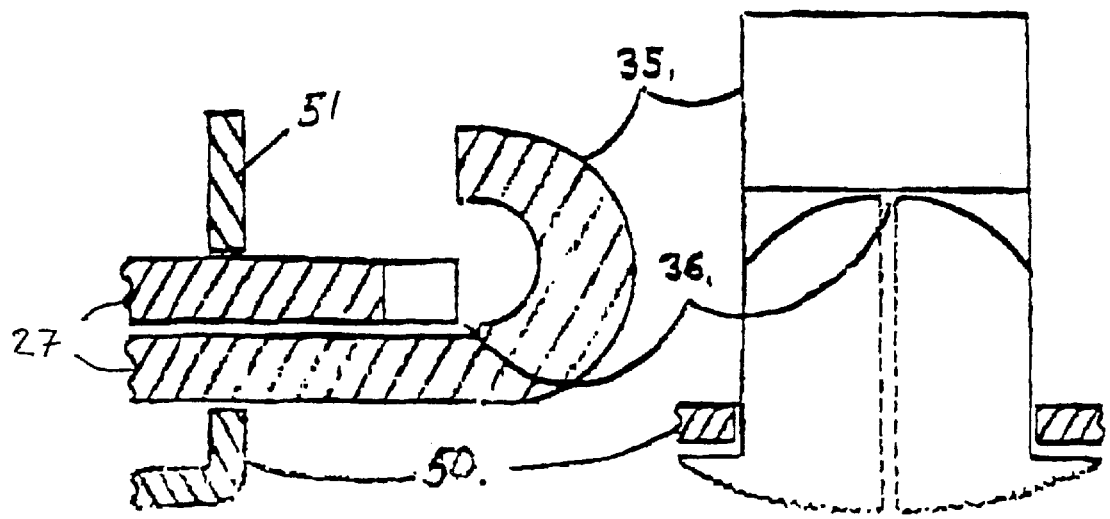
FIG. 8 shows a detail of a delivery opening,according to a preferred embodiment of the invention.

A preferred embodiment of the dispenser module according to the present invention provided with connecting means integrated with the drug supplying means and also provided with preferred arrangements of delivery channels will know be described with references to FIGS. 6–8. FIG. 6 discloses a cross-sectional view of a connecting nipple 25 of the dispenser module 3. This connecting nipple is adapted to cooperate with the nipple on the reservoir module and is preferably threaded and made in the same material as the reservoir nipple. Two stop protrusions 26 are arranged for engagement with the corresponding protrusions 16 on the reservoir module in order to prevent the dispenser and reservoir modules to be disconnected when once connected together. Two parallel plates 27 are joined together so that the drug delivery channels are provided between these plates. There are many different ways to provide a predetermined grooved pattern in each plate that corresponds to the desired delivery channels. These are etching, engraving, cutting or similar processes. The plates are preferably made of titanium, gold, ceramic material, silicon, stainless steel or a polymer, e.g. PVC. The connecting nipple 25 also comprises a membrane block 28 with two membranes 29 made of an inert material attached to the membrane block by shrinkage fit. The above-mentioned different parts forming the connecting nipple are welded together under pressure in order to prevent any leakage in the assembled implanted system. The lower side of the connecting nipple is provided with a lower supporting part 30 to support a lower protecting casing 50 of the dispenser module. Similarly, the upper side of the connecting nipple is provided with an upper supporting part 31 to support an upper protecting casing 51 of the dispenser module. The upper and lower casings are made of an inert material and are fastened to the connecting nipple by e.g. welding. FIG. 7 shows a top view of the dispenser module according to a preferred embodiment of the invention. Four drug delivery openings 5 are arranged evenly distributed along the periphery of the dispenser module. Four delivery channels, indicated by dotted lines, supply the openings with a drug liquid. The upper membrane of the two membranes 29 is also disclosed. In order to guide the tip of a syringe when filling or refilling the implant with a drug two magnets 33 are arranged on the upper side of the dispenser module, either integrated in the connecting nipple or in the upper protective casing. A detector that detects the magnet fields from the magnet is connected to an apparatus for guiding the tip of the syringe to the correct position above the membrane 29.

FIG. 8 shows in great detail one of the delivery openings according the preferred embodiment of the present invention. The joined plates 27 extend outside the upper and lower protecting casing 50,51. One of the plates 35 is bent around the rounded end of the other plate so that the outflow opening 36 is protected against pressure from the tissue that might reduce or stop the outflow. The outflow is arranged at the peak of the rounded end of the other plate in order to avoid that drug liquid is accumulated around the outflow opening 36.

An alternative embodiment of the dispenser module according to the present invention provided with connecting means integrated with the drug supplying means and also provided with preferred arrangements of delivery channels will know be described with references to FIGS. 9–12.

Figure 9:
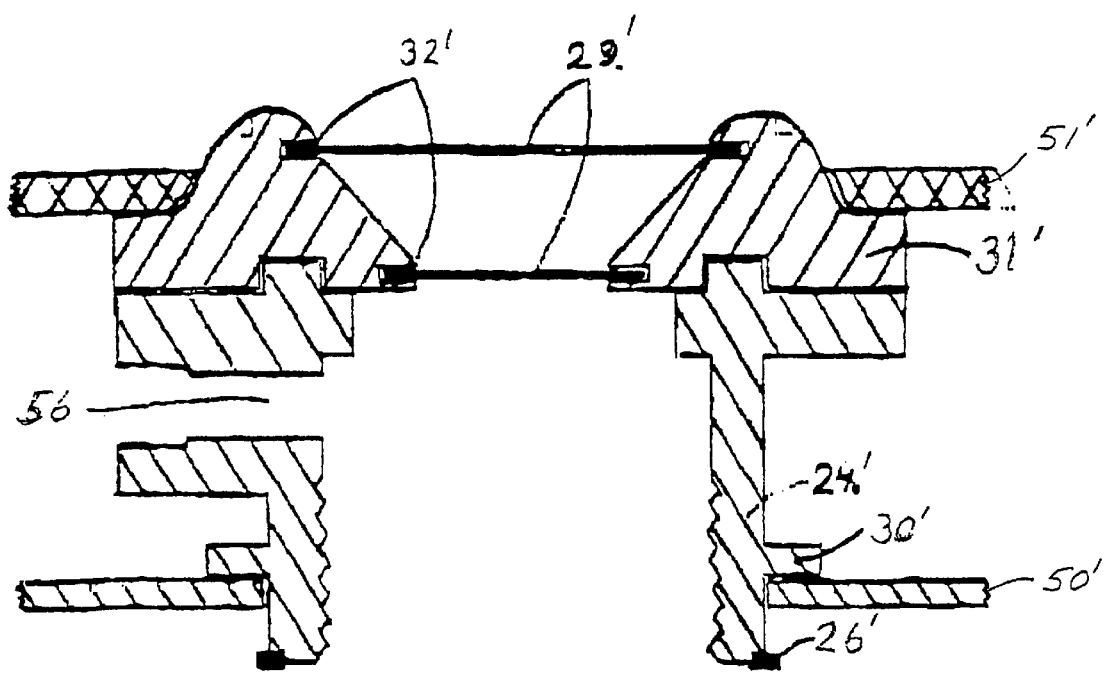
FIG. 9 shows a cross-sectional view of an alternative embodiment of a connecting nipple of the dispenser module according to the present invention.

FIG. 9 discloses a cross-sectional view of a connecting nipple of the dispenser module. This connecting nipple is adapted to cooperate with the nipple on the reservoir module and is preferably threaded and made in the same material as the reservoir nipple. Two stop protrusions 26' are arranged for engagement with the corresponding protrusions 16 on the reservoir module in order to prevent the dispenser and reservoir modules to be disconnected when once connected together. The connecting nipple also comprises a membrane block 28' with two membranes 29' made of an inert material attached to the membrane block by shrinkage fit 32'. The above-mentioned different parts forming the connecting nipple are welded together under pressure in order to prevent any leakage in the assembled implanted system. The lower side of the connecting nipple is provided with a lower supporting part 30' to support a lower protecting casing 50' of the dispenser module. Similarly, the upper side of the connecting nipple is provided with an upper supporting part 31' to support an upper protecting casing 51' of the dispenser module. The upper and lower casings are made of an inert material and are fastened to the connecting nipple by e.g. welding. The embodiment described in connection with FIG. 9 differs from the one described in connection with FIG. 6 in that a connection 56 is provided, e.g. on the side of the connection nipple, where a pump (not shown) is arranged instead of a direct connection of a delivery channel (formed e.g. by plates 27 in FIG. 6). The pump receives via opening 56 a flow of drug liquid from the reservoir module and is on its other side (downstream) connected to delivery channels, e.g. formed by plates as in FIGS. 6–8.

Figure 10:
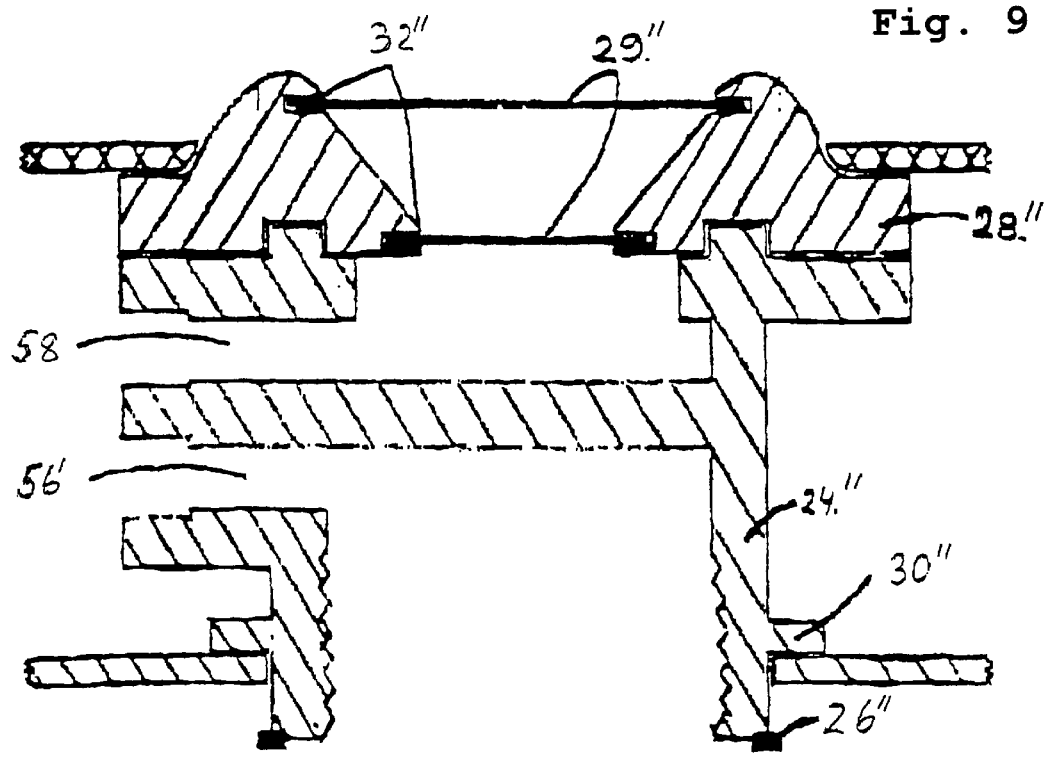
FIG. 10 shows a cross-sectional view of a second alternative embodiment of a connecting nipple of the dispenser module according to the present invention.

FIG. 10 discloses a cross-sectional view of a connecting nipple of still another alternative embodiment of the dispenser module. In addition to the connecting nipple described in connection with FIG. 9 an additional connection 58 is arranged, e.g. on the side of the nipple, for connection of a second pump. This pump is activated when filling or refilling the reservoir module.

Figure 11:
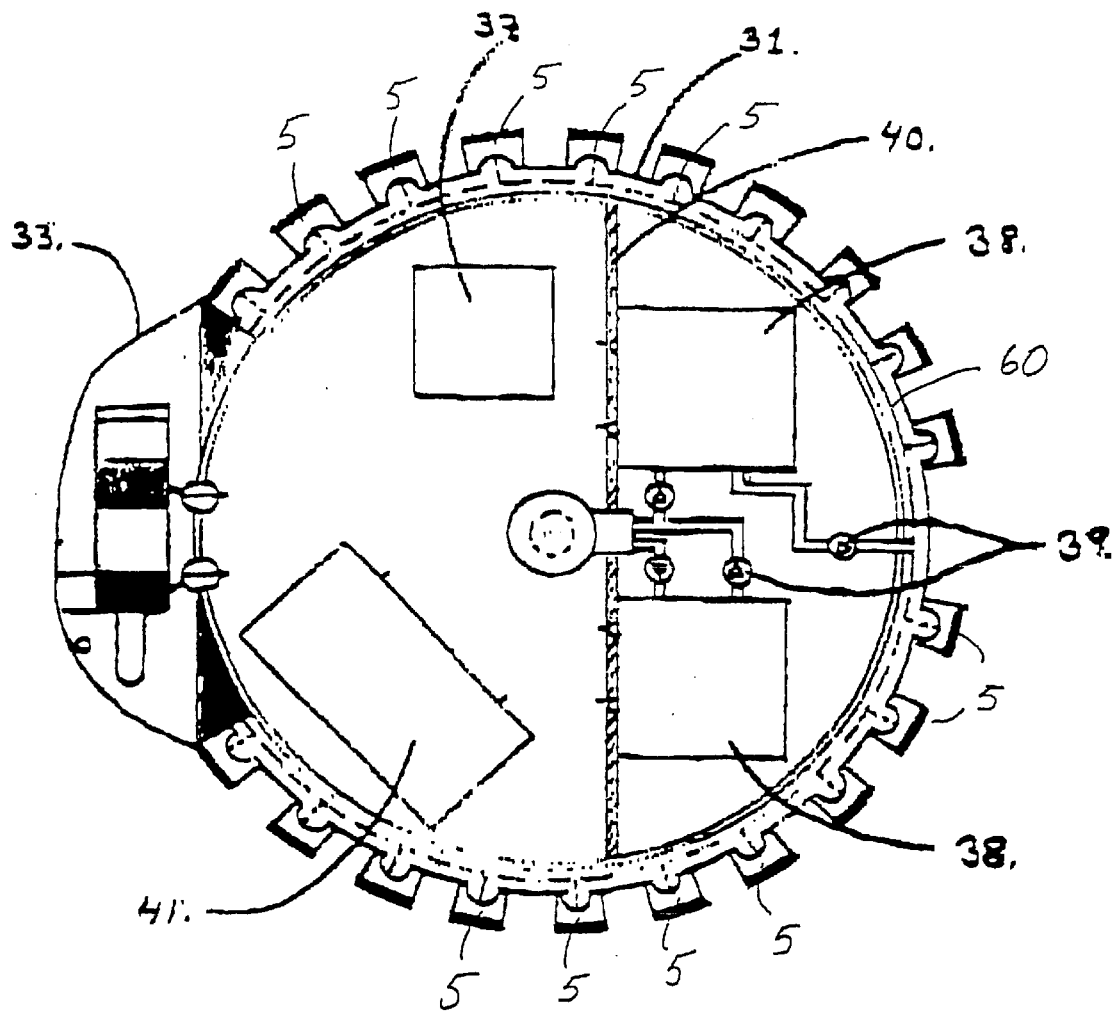
FIG. 11 shows a top view of the dispenser module according to a second preferred embodiment of the present invention.

FIG. 11 shows a top view of the dispenser module according to a second preferred embodiment of the invention. Several delivery openings 5 are arranged along the periphery of the dispenser module. A drug supplying channel 60 runs along the periphery, close to the delivery openings, of the dispenser module in order to supply the openings with a drug liquid. This drug supplying channel is provided with the drug liquid from the reservoir module. This can be performed by connecting the periphery drug supplying channel 60 to the channel(s) formed by the plates 27 as described in connection with FIG. 6. Alternatively it is connected to one or many pumps 38 as illustrated in FIG. 11. The embodiment disclosed in FIG. 11 further comprises a control unit 37, a power supply 41, e.g. a battery, and one or many valves 39. A separating wall 40 is arranged to separate the "wet" part of the module from the control unit and the power supply. A connection part 33 for connection of a sensor or a heart stimulating electrode (e.g. according to the IS-standard) can also be arranged on the dispenser module.

Figure 12:
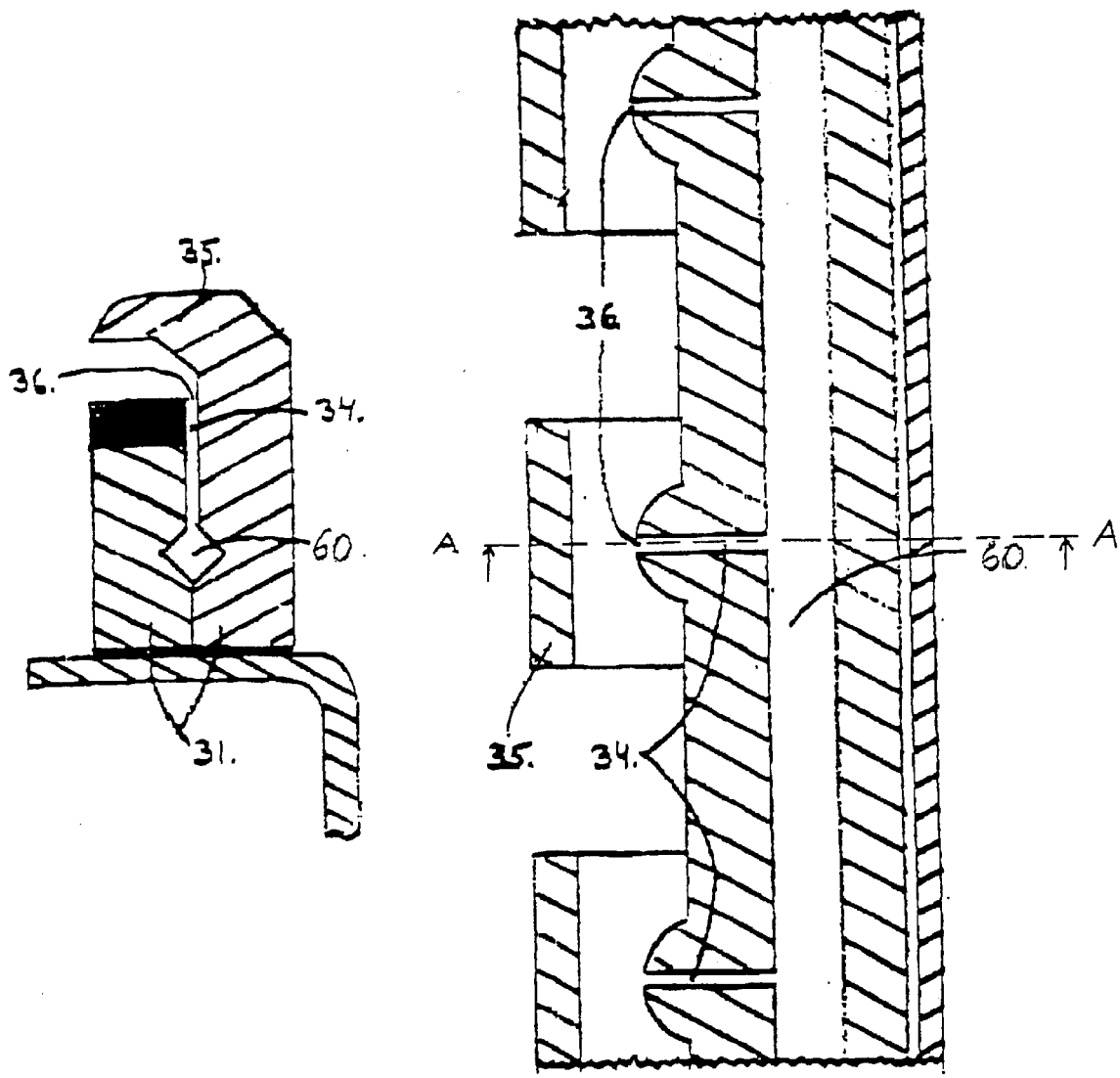
FIG. 12 shows a detail of delivery openings according to a second preferred embodiment of the invention.

FIG. 12 shows in greater detail the delivery openings according the embodiment of the present invention described in FIG. 11. The right drawing shows a cross-sectional view of the periphery drug supplying channel 60 and three delivery openings. The left drawing shows a cross-sectional view of a delivery opening along line A—A of the right drawing.

The periphery drug supplying channel 60 and the delivery openings are preferably arranged inside a plate arrangement running along the periphery of the module. The plate arrangement comprises two joined plates 31 that are joined together so that the periphery drug delivery channel 60 and the outflow channels 34 to the delivery openings 36 are provided between these plates. There are many different ways to provide a predetermined grooved pattern in each plate that correspond to the desired delivery channels. These are etching, engraving, cutting or similar processes. The plates are preferably made of titanium, gold, ceramic material, silicon, stainless steel or a polymer, e.g. PVC. One of the plates 35 is bent around the rounded end of the other plate so that the outflow opening 36 is protected against pressure from the tissue that might reduce or stop the outflow. The outflow is arranged at the peak of the rounded end of the other plate in order to avoid that drug liquid is accumulated around the outflow opening 36. The outflow channels 34 from the periphery drug supplying channel to the delivery openings are provided with an increasing cross-sectional area depending on the distance from reservoir module in order to be able to deliver the same volume from each delivery opening (see description in connection with FIG. 5).

Below is a description of a method of using an implantable drug delivery system according to the present invention.

Depending of the therapy prescribed to a patient, e.g. the treatment duration, social situation for the patient, the prescribed dosage, etc., a matching pair of reservoir and dispenser modules is chosen. The drug outflow per time unit for a particular dispenser module can be calculated based on the number of delivery openings, the cross-sectional area of the drug delivery channels and the viscosity for the drug liquid. The higher dosing volume the more delivery openings in order to minimize the dosing volume delivered at each opening per time unit. The cross-sectional area of an outflow channel is typically in the range of 0,01 mm to 0,1 mm. The flow-rate of the dispenser module is typically in the range of 8–12 $\mu$l/hour. The volume of the inner reservoir is typically in the range 4–30 ml.

The dispenser module is connected to the reservoir module via the threaded nipples by rotating the modules relative each other until the stop protrusion engages. A needle of a syringe, filled with a drug, penetrates the membranes of the dispenser module and opens the valve by moving valve part 19 to its lower position. The inner reservoir of the reservoir module is then filled due to the under-pressure exerted by the vacuum inside the inner reservoir. When the inner reservoir is filled with a drug, the drug expelling means, e.g. plates and one or many springs, exert a force on the inner reservoir that increases the pressure inside the reservoir. The inner reservoir then expels the drug liquid to the drug delivery channels of the dispenser module and thus to the tissue near the implanted system. This situation persists until the inner reservoir is so compressed that the pressure inside the reservoir is less than the counter pressure from the tissue near the delivery openings. It is then possible to refill the reservoir module and the above procedure is repeated.

The present invention is not limited to the above-described preferred embodiments. Various alternatives, modifications and equivalents may be used. Therefore, the above embodiments should not be taken as limiting the scope of the invention, which is defined by the appending claims.

What is claimed is:

1. Implantable drug delivery system comprising a reservoir module provided with a drug reservoir and a drug expelling means arranged to expel a drug from said drug reservoir to a dispenser module for delivering the drug to tissue, characterized in that said modules are physically separate parts and that said reservoir module is provided with a first connecting means and said dispenser module is provided with a second connecting means, wherein, at the time of implantation, said reservoir and dispenser modules are adapted to be connected together by said first and second connecting means.

2. System according to claim 1 characterized in that said first connecting means comprises a reservoir nipple and that said second connecting means comprises a connecting nipple wherein the reservoir module supplies said dispenser module with the drug liquid via said nipples.

3. System according to claim 1 characterized in that said reservoir module comprises drug supplying means adapted to be coupled to the dispenser module in order to supply the dispenser module with the drug from the reservoir module.

4. System according to claim 1 characterized in that said dispenser module is provided with a predetermined number of drug delivery openings, wherein said predetermined number is at least two.

5. System according to claim 4 characterized in that the openings of the dispenser module are arranged on the part of the dispenser module adapted to be in contact with tissue.

6. System according to claim 4 in that the openings of the dispenser module are arranged along the periphery of the dispenser module.

7. System according to any of claim 4 in that said predetermined number of delivery openings is four.

8. System according to any of claim 4 in that said predetermined number of delivery openings lies in the interval 10–30.

9. Method of administrating a drug liquid to a patient using an implantable drug delivery system according to of claim 1 characterized in that said method comprising the following steps:
   i) choosing a dispenser module and a reservoir module having predetermined characteristics depending on the prescribed therapy of the patient;
   ii) connecting the chosen modules to each other;
   iii) implanting the system at a patient location where the drug should be administrated.

10. Method according to claim 9 characterized in that said method further comprising the following step:
   iv) filling or refilling the reservoir module with a drug liquid when necessary.

* * * * *